United States Patent
Cooper et al.

(10) Patent No.: US 6,548,243 B1
(45) Date of Patent: Apr. 15, 2003

(54) (CAG)/Q EXPANSION DISORDERS

(75) Inventors: Arthur J. L. Cooper, Croton on Hudson, NY (US); John P. Blass, Bronxville, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/743,590

(22) PCT Filed: Jul. 14, 1999

(86) PCT No.: PCT/US99/15899

§ 371 (c)(1),
(2), (4) Date: Mar. 13, 2001

(87) PCT Pub. No.: WO00/03739

PCT Pub. Date: Jan. 27, 2000

Related U.S. Application Data (60) Provisional application No. 60/092,845, filed on Jul. 14, 1998.

(51) Int. Cl.$^7$ ................................................ C12Q 1/00
(52) U.S. Cl. .................................. 435/4; 435/6; 435/15
(58) Field of Search .................... 435/4, 6, 15; 536/23.2

(56) References Cited

U.S. PATENT DOCUMENTS 5,723,301 A * 3/1998 Burke et al. ................. 435/7.1
5,750,360 A * 5/1998 Fesus et al. ................... 435/23
5,834,183 A * 11/1998 Orr et al. ........................ 435/6

OTHER PUBLICATIONS

Fesus L. Transglutaminase Catalyzed Protein Cross Linking . . . Cellular and Molecular Neurobiology 18(6)683–694, 1998.*
Cooper A. Polyglutamine Domains are Substrates of Tissue Transglutaminase. J of Neurchemistry 69(1)431–434, 1997.*

* cited by examiner

*Primary Examiner*—Ralph Gitomer
(74) *Attorney, Agent, or Firm*—Nixon Peabody LLP (57) ABSTRACT

A method of diagnosing a $(CAG)_n/Q_n$-expansion disorder in an individual, said method including: obtaining a sample from an individual; combining the sample with o-phthaldialdehyde under conditions effective to form a test solution comprising an o-phthaldialdehyde derivative of $N^\epsilon$-(L-γ-glutamyl)-L-lysine; and determining whether the test solution contains a concentration of the o-phthaldialdehyde derivative of $N^\epsilon$-(L-γ-glutamyl)-L-lysine which is elevated in comparison to a normal concentration of the o-phthaldialdehyde derivative of $N^\epsilon$-(L-γ-glutamyl)-L-lysine, wherein an elevated concentration in the test solution indicates that the individual has a $(CAG)_n/Q_n$-expansion disorder. Also disclosed are methods of measuring progression of a $(CAG)_n/Q_n$-expansion disorder and measuring therapeutic efficacy of a treatment for a $(CAG)_n/Q_n$-expansion disorder.

20 Claims, 2 Drawing Sheets

(CAG)/Q EXPANSION DISORDERS

This application is a 371 of PCT/US/99/15899 filed Jul. 14, 1999 which claims the benefit of U.S. Provisional Patent Application Serial No. 60/092,845, filed Jul. 14, 1998.

This invention was made in part with support by the U.S. Government under Grant No. 5R35 AG09014 (Lead Award) from the National Institute of Health. The U.S. Government may have certain rights in this invention.

BACKGROUND OF THE INVENTION

Huntington disease (HD) was the first disorder shown to be due to an expansion of a $(CAG)_n$ tract within exon 1 of the affected gene and to a resultant increase in length of a $Q_n$ domain within the corresponding encoded protein, huntingtin (Huntington's Disease Collaborative Research Group, "A Novel Gene Containing a Trinucleotide Repeat that is Expanded and Unstable on Huntington's Disease Chromosome," Cell 72:971–983 (1993)). Subsequently, seven other neurodegenerative diseases, including dentatorubral pallidoluysian atrophy, spinobulbar muscular atrophy, and spinocerebellar ataxis 1, 2, 3, 6 and 7, have been shown to be caused by pathological $(CAG)_n/Q_n$-expansions (Lunkes et al., "Polyglutamines, Nuclear Inclusions and Degenerations," Nat. Med. 3:1201–1202 (1997)). Green was the first to suggest that transglutaminase(s) may play a role in trinucleotide-repeat diseases (Green, "Human Genetic Diseases Due to Codon Reiteration: Relationship to an Evolutionary Mechanism," Cell 74:955–956 (1993)). Others have also suggested that transglutaminase activity may be a factor in the etiology of $(CAG)_n/Q_n$-expansion diseases (Lorand, L., "Neurodegenerative Diseases and Transglutaminase," Proc. Natl. Acad. Sci. USA 93:14310–14313 (1996); Cooper et al., "Polyglutamine Domains are Substrates of Tissue Transglutaminase. Does Transglutaminase Play a Role in Expanded CAG/poly-Q Neurodegenerative Diseases?," J. Neurochem. 69:431–434 (1997)) and in the formation of proteinaceous deposits in the brains of Alzheimer disease patients (Selkoe et al., "Alzheimer's Diseases: Insolubility of Partially Purified Helical Filaments in Sodium Dodecyl Sulfate and Urea," Science 215:1243–1245 (1982) and Johnston et al., "Transglutaminase Activity is Increased in Alzheimer's Disease Brain," Brain Res. 751:323–329 (1997)). In support of the idea that transglutaminases may be involved in $(CAG)_n/Q_n$-expansion diseases, $Q_n$ domains, whether flanked by small numbers of amino acids (Kahlem et al., "Peptides Containing Glutamine Repeats are Substrates for Transglutaminase-catalyzed Cross-linking: Relevance to Diseases of the Nervous System," Proc. Natl. Acad. Sci. USA 93:14580–14585 (1996) and Kahlem et al., "Transglutaminase Action Imitates Huntington's Disease: Selective Polymerization of Huntington Containing Polyglutamine," Mol. Cell 1:595–601 (1998)), or embedded within full-length protein constructs (Cooper et al., "Polyglutamine Domains are Substrates of Tissue Transglutaminase. Does Transglutaminase Play a Role in Expanded CAG/poly-Q Neurodegenerative Diseases?," J. Neurochem. 69:431–434 (1997) and Cooper et al., "Transglutaminase-catalyzed Inactivation of Glyceraldehyde 3-Phosphate Dehydrogenase Complex by Polyglutamine Domains of Pathological Length," Proc. Natl. Acad. Sci. USA 94:12604–12609 (1997)), are excellent substrates of tissue transglutaminase. It has been also shown that the ability of "naked" $Q_n$ domains to act as Q-donor substrates of tissue transglutaminase increases in the order $Q_{20} < Q_{40} < Q_{60}$ (Gentile et al., "Tissue Transglutaminase-catalyzed Formation of High-Molecular-Weight Aggregates In Vitro is Favored with Long Polyglutamine Domains: A Possible Mechanism Contributing to CAG-triplet Diseases," Arch. Biochem. Biophys. 352:314–321 (1998)). Moreover, the substrate activity per individual Q residue is greater for $Q_{60}$ than for $Q_{20}$ (Gentile et al., "Tissue Transglutaminase-catalyzed Formation of High-Molecular-Weight Aggregates In Vitro is Favored with Long Polyglutamine Domains: A Possible Mechanism Contributing to CAG-triplet Diseases," Arch. Biochem. Biophys. 352:314–321 (1998)). Importantly, Kahlem et al. showed that huntingtin containing a pathological-length $Q_n$ domain is a much better substrate of commercial guinea pig liver tissue transglutaminase and of crude brain tissue transglutaminase than is huntingtin containing a non-pathological-length $Q_n$ domain (Kahlem et al., "Transglutaminase Action Imitates Huntington's Disease: Selective Polymerization of Huntington Containing Polyglutamine," Mol. Cell 1:595–601 (1998)). Thus, pathological-length $Q_n$ domains may be synergistically better substrates of tissue transglutaminase than are non-pathological-length $Q_n$ domains.

Transglutaminase activity is known to be present in both the cytosolic and nuclear fractions of a variety of cells, including brain cells (Singh et al., "Identification and Characterization of an 80 Kilodalton GTP-binding Protein/Transglutaminase from Adult Rabbit Liver Nuclei," Biochemistry 34:15863–15871 (1995); and Lesort et al., "Distinct Nuclear Localization and Activity of Transglutaminase," J. Biol. Chem. 273:11991–11994 (1998)). These are the same compartments in which aggregates are formed in affected brain cells.

A method for diagnosing HD or a predisposition to develop HD involves determining the number of $(CAG)_n$ repeats present in the huntingtin gene of a patient. This method is performed by using a fragment of a nucleic acid encoding hungtingtin in a gene amplification assay or other nucleic hybridization assays. This methodology is disclosed, for example, in U.S. Pat. Nos. 5,693,757 and 5,686,288 to MacDonald et al.

However, as noted above, there are a number of $(CAG)_n/Q_n$-expansion diseases, all of which involve different genes and proteins. Diagnostic procedures using nucleic acids for one $(CAG)_n/Q_n$-expansion disease would not necessarily identify all diseases. Rather than rely on a battery of nucleic acid-based procedures to diagnose a $(CAG)_n/Q_n$-expansion disease, a single diagnostic analysis would be beneficial. In particular, it would be beneficial to obtain a quick and reliable method of diagnosing $(CAG)_n/Q_n$ expansion disorders, including disease stages, and assessing the efficacy of therapeutic treatments of the $(CAG)_n/Q_n$ expansion disorders. The present invention overcomes these and other deficiencies in the prior art.

SUMMARY OF THE INVENTION

One aspect of the present invention relates to a method of diagnosing a $(CAG)_n/Q_n$-expansion disorder in an individual. This method is performed by obtaining a sample from an individual and determining whether the sample contains a concentration of $N^\epsilon$-(L-γ-glutamyl)-L-lysine which is elevated in comparison to a normal concentration of $N^\epsilon$-(L-γ-glutamyl)-L-lysine.

Another aspect of the present invention relates to a method of measuring progression of a $(CAG)_n/Q_n$-expansion disorder (i.e., for individuals previously diagnosed with a $(CAG)_n/Q_n$-expansion disorder). This method is performed by obtaining a first sample from an individual, determining a first concentration, of $N^\epsilon$-(L-γ-glutamyl)-L- lysine in the first sample, obtaining a second sample from the individual at a time after the first sample is obtained, and determining a second concentration of $N^\epsilon$-(L-γ-glutamyl)-L-lysine in the second sample. Progression of the $(CAG)_n/Q_n$-expansion disorder is indicated by the second concentration being higher than the first concentration.

Still another aspect of the present invention relates to a method of measuring therapeutic efficacy of a treatment for a $(CAG)_n/Q_n$-expansion disorder. This method is performed by obtaining a first sample from an individual, determining a first concentration of $N^\epsilon$-(L-γ-glutamyl)-L-lysine in the first sample, providing the individual with a treatment for a $(CAG)_n/Q_n$-expansion disorder, obtaining a second sample from the individual after providing the individual with the treatment, determining a second concentration of $N^\epsilon$-(L-γ-glutamyl)-L-lysine in the second sample, and comparing the second concentration to the first concentration to measure the therapeutic efficacy of the treatment for a $(CAG)_n/Q_n$-expansion disorder.

As indicated previously, there are currently a number of diseases or disorders that have been classified as $(CAG)_n/Q_n$-expansion disorders, particularly neurodegenerative diseases. Each year, numerous patients are diagnosed with these and other various neurodegenerative diseases. The present invention provides a reliable method of diagnosing whether an individual suffers from a $(CAG)_n/Q_n$-expansion disorder, as well as the progression thereof, and any treatments thereof.

DETAILED DESCRIPTION OF THE INVENTION

One aspect of the present invention relates to a method of diagnosing a $(CAG)_n/Q_n$-expansion disorder in an individual. This method is performed by obtaining a sample from an individual and determining whether the sample contains a concentration of $N^\epsilon$-(L-γ-glutamyl)-L-lysine which is elevated in comparison to a normal concentration of $N^\epsilon$-(L-γ-glutamyl)-L-lysine. According to this first aspect of the present invention, the concentration of $N^\epsilon$-(L-γ-glutamyl)-L-lysine in a sample from an individual is compared to a standard or normal $N^\epsilon$-(L-γ-glutamyl)-L-lysine concentration which is expected for persons who are negative for a $(CAG)_n/Q_n$-expansion disorder.

Since transglutaminase(s) are an important factor in $(CAG)_n/Q_n$-expansion diseases, increased formation of proteins cross-linked by $N^\epsilon$-(γ-L-glutamyl)-L-lysine linkages should occur in tissues of patients with these neuropathies. If some of the cross-linked proteins remain soluble long enough to be degraded by proteasomes, increased cellular formation of free $N^\epsilon$-(γ-L-glutamyl)-L-lysine should also ensue.

Theoretically, γ-glutamyl lysine could also be generated by γ-glutamyl transpeptidase (Eq. 1), where L-amino acid is L-lysine.

(Eq. 1)

However, L-lysine has not been described as a substrate of the enzyme (Orlowski et al, "γ-Glutamyl-p-nitroanilide: A New Convenient Substrate for Determination and Study of L- and D-γ-glutamyltranspeptidase Activities," *Biochem. Biophys. Acta* 73:679–681 (1963) and Meister et al., *Ann. Rev. Biochem.* 52:711–760 (1983)., which is hereby incorporated by reference). Moreover, even if γ-glutamyl transpeptidase were to accept L-lysine, coupling would be at the a-nitrogen of this amino acid, affording $N^\alpha$-(L-γ-glutamyl)-L-lysine (the $N^\alpha$-positional isomer) rather than the $N^\epsilon$-positional isomer.

$N^\epsilon$-(L-γ-glutamyl)-L-lysine is resistant to proteolysis. In fact, only one route for the disposal of this dipeptide is known. $N^\epsilon$-(L-γ-glutamyl)-L-lysine is an excellent substrate of L-γ-glutamylamine cyclotransferase (Eq. 2) (Fink et al., "γ-Glutamylamine Cyclotransferase: Specificity Toward ε-(L-γ-glutamyl)-L-lysine and Related Compounds," *Proc. Natl. Acad. Sci. USA* 77:4564–4568 (1980) and Fink et al., "γ-Glutamylamine Cyclotransferase: An Enzyme Involved in the Catabolism of ε-(L-γ-glutamyl)-L-lysine and other γ-glutamylamines," *Mol. Cell Biochem.* 38:59–67 (1981), which are hereby incorporated by reference).

(Eq. 2)

The amine portion of the substrate can be lysine (bound at the ε-nitrogen) or a variety of amines, diamines, and polyamines (Fink et al., "γ-Glutamylamine Cyclotransferase: Specificity Toward ε-(L-γ-glutamyl)-L-lysine and Related Compounds," *Proc. Natl. Acad. Sci. USA* 77:4564–4568 (1980); Fink et al., "γ-Glutamylamine Cyclotransferase: An Enzyme Involved in the Catabolism of $N^\epsilon$-(L-γ-glutamyl)-L-lysine and other γ-glutamylamines," *Mol. Cell Biochem.* 38:59–67 (1981); Fink et al., "γ-Glutylamine Cyclotransferase (Rabbit Kidney)," *Methods Enzymol.* 94:347–351 (1983); and Fink et al., "Enzymic Cleavage of γ-Glutamylpolyamines: Implications in the Degradation of Polyamine-protein Conjugates," *Adv. Polyamine Res.* 3:187–196 (1981), which are hereby incorporated by reference). L-γ-glutamylamine cyclotransferase is distinct from the more well known (L-γ-glutamyl)-L-amino acid cyclotransferase (Eq. 3)—a component of the γ-glutamyl cycle (Fink et al., "γ-Glutylamine Cyclotransferase (Rabbit Kidney)," *Methods Enzymol.* 94:347–351 (1983) and Fink et al., "Enzymic Cleavage of γ-Glutamylpolyamines: Implications in the Degradation of Polyamine-protein Conjugates," *Adv. Polyamine Res.* 3:187–196 (1981), which is hereby incorporated by reference).

(Eq. 3)

(L-γ-Glutamyl)-L-amino acid cyclotransferase acts almost exclusively on L-γ-glutamyl compounds in which amide linkage is through the γ-carboxyl of glutamate and α-nitrogen of the L-amino acid moiety. Therefore, $N^\alpha$-(L-γ-glutamyl)-L-lysine should not be a substrate of (L-γ-glutamyl)-L-amino acid cyclotransferase, because amide linkage in this compound is through the ε-nitrogen of lysine rather than through the α-nitrogen.

Although γ-glutamylamine cyclotransferase activity is widely distributed in mammalian tissues, it is most prevalent in kidney with much lower levels in brain (Fink et al., "γ-Glutylamine Cyclotransferase: Specificity Toward $N^\epsilon$-(L-γ-glutamyl)-L-lysine and Related Compounds," *Proc. Natl. Acad. Sci. USA* 77:4564–4568 (1980), which is hereby incorporated by reference). Taken together, the evidence suggests that $N^\epsilon$-(L-γ-glutamyl)-L-lysine should be a biochemical marker for transglutaminase activity. Moreover, because of the limited activity in the brain of the only enzyme significantly able to break down $N^\epsilon$-(L-γ-glutamyl)-

L-lysine, the concentration of this compound is likely to be elevated in brain tissue or cerebrospinal fluid ("CSF") of patients with $(CAG)_n/Q_n$-expansion diseases.

Any fluid sample containing $N^\epsilon$-(L-γ-glutamyl)-L-lysine can be obtained from an individual for analysis according to the present invention. Exemplary fluid samples are those obtained from cerebrospinal fluid, blood, and urine. Of these, cerebrospinal fluid is preferred since it is believed to contain $N^\epsilon$-(L-γ-glutamyl)-L-lysine resulting primarily, if not exclusively, from the activity of transglutaminase in neuro-tissues of the brain and/or central nervous system.

Any suitable method of determining the concentration of $N^\epsilon$-(L-γ-glutamyl)-L-lysine can be performed. Exemplary methods include, but are not limited to, (1) isotope dilution gas chromatography-mass spectrometry ("GC-MS") analysis with a labeled standard (Moore et al., "The Use of Isotope Dilution Mass Spectrometry for the Certification of Standard Reference Materials," *Environment International* 10:169–173 (1984), and Fassett et al., "Isotope Dilution Mass Spectrometry for Accurate Elemental Analysis," *Analytical Chemistry* 61: 386–390 (1989), which are hereby incorporated by reference), (2) high performance liquid chromatography ("HPLC") of the o-phthaldialdehyde derivative (Venema et al., "Automated Precolumn Derivatization Device to Determine Neurotransmitter and Other Amino Acids by Reversed-phase High-performance Liquid Chromatography," *J. Chromatogr.* 260(2):371–376 (1983); Jones and Gilligan, "o-Phthaldialdehyde Precolumn Derivatization and Reversed-phase High-performance Liquid Chromatography of Polypeptide Hydrolysates and Physiological Fluids," *J. Chromatogr.* 266:471–482 (1983); and Fleury and Ashley, "High-performance Liquid Chromatographic Analysis of Amino Acids in Physiological Fluids: On-line Precolumn Derivatization with o-phthaldialdehyde." *Anal. Biochem.* 133(2):330–335 (1983), which are hereby incorporated by reference), (3) hydrolysis with γ-glutamylamine cyclotransferase followed by HPLC analysis of lysine or 5-oxoproline products, (4) HPLC analysis with coularray detection (see, e.g., Hudson et al., "Age-associated Change in Mitochondrial DNA Damage," *Free Radic. Res.* 9(6):573–579 (1998), which is hereby incorporated by reference), and (5) GC-MS analysis with unlabeled internal standard. Of these, the isotope dilution GC-MS analysis is preferred.

Isotope dilution GC-MS involves the use of an isotope standard that is introduced in a known quantity to the GC-MS. The fundamental principle behind isotope dilution analysis is the constant elemental isotopic ratio. By artificially altering the total amount of an element with an enriched isotope, analysis of the concentration of an element is measured from the isotopic ratio, given the total amount measured and the known amount of the enriched isotope. The measurement employs a mass spectrometer to determine the isotopic ratio. Using the isotopic ratio, it is possible to calculate the unknown starting concentration of an element since the quantity of isotope introduced into the sample is known. Examples of isotope dilution analysis for total elemental concentration are described for standard reference materials and for general analysis using thermal isotope dilution mass spectrometry (Moore et al., "The Use of Isotope Dilution Mass Spectrometry for the Certification of Standard Reference Materials," *Environment International* 10:169–173 (1984), and Fassett et al., "Isotope Dilution Mass Spectrometry for Accurate Elemental Analysis," *Analytical Chemistry* 61: 386–390 (1989), which are hereby incorporated by reference). A method of speciated isotope dilution mass spectrometry is described in U.S. Pat. No. 5,414,259 to Kingston, which is hereby incorporated by reference. By way of example, specific analysis of total chromium and selenium and other metals by this method of isotope dilution mass spectrometry using a GC-MS are described in the literature (Reamer and Veillon, "A Double Isotope Dilution Method for Using Stable Selenium Isotopes in Metabolic Tracer Studies: Analysis by Gas Chromatography/Mass Spectrometry (GC/MS)," *J. Nutrition* 113:786–792 (1983); Reamer and Veillon, "Determination of Selenium in Biological Materials by Stable Isotope Dilution Gas Chromatography-Mass Spectrometry," *Analytical Chemistry* 53: 2166–2169,(1981); and Veillon et al., "Determination of Chromium in Biological Materials by Stable Isotope Dilution," *Analytical Chemistry* 51:1022–1024 (1979), which are hereby incorporated by reference). Isotope dilution has been employed previously in diagnostic procedures for detecting conditions indicative of atherosclerosis (see U.S. Pat. No. 5,731,208 to Heinecke, which is hereby incorporated by reference).

To perform an isotope dilution GC-MS analysis, the sample must be prepared prior to its analysis. This involves preparing a test solution (i.e., which will be introduced into a gas chromatograph column) for analysis. The test solution is prepared by combining the sample and an internal standard. Any compound containing an elemental isotope can be used as the internal standard. The elemental isotope (of the compound used as the internal standard) can have an atomic weight which is heavier or lighter than normal. A number of elemental isotopes can be utilized such as, for example, $^2H$, $^{13}C$, and $^{15}N$. In addition, the elemental isotope can be a radio-isotope (see Duffy et al., "Identification of α-ketoglutaramate in Rat Liver, Kidney, and Brain: Relationship to Glutamine Transaminase and ω-amidase Activities." *J. Biol. Chem.* 250:527–532 (1974), which is hereby incorporated by reference), although radioactivity of the compound is not required for its use as the internal standard. A preferred internal standard for purposes of measuring $N^\epsilon$-(L-γ-glutamyl)-L-lysine is a isotope-labeled $N^\epsilon$-(L-γ-glutamyl)-L-lysine, more preferably $N^\epsilon$-(L-γ-glutamyl)-L-[α-$^{15}N$]lysine.

Prior to GC-MS analysis, the internal standard (e.g., isotope-labeled $N^\epsilon$-(L-γ-glutamyl)-L-lysine) is added in a known amount to samples, which are then prepared for GC-MS analysis. The use of isotope-labeled $N^\epsilon$-(L-γ-glutamyl)-L-lysine as internal standard in GC-MS analysis takes advantage of the fact that any losses of $N^\epsilon$-(L-γ-glutamyl)-L-lysine in extraction, subsequent treatment, and transferring processes will also result in similar losses of isotope-labeled $N^\epsilon$-(L-γ-glutamyl)-L-lysine. Therefore, while other compounds (i.e., $N^\epsilon$-(L-γ-glutamyl)-L-lysine analogs) can be used as internal standards, isotope-labeled $N^\epsilon$-(L-γ-glutamyl)-L-lysine is more reliable.

Further preparation of the test sample includes introducing L-γ-glutamylamine cyclotransferase into the test solution prior to GC-MS analysis. Preferably the L-γ-glutamylamine cyclotransferase is purified according to the methods of Fink and Folk (Fink and Folk, "γ-Glutamylamine Cyclotransferase (rabbit kidney)," *Methods Enzymol.* 94:347–351 (1983), which is hereby incorporated by reference). As indicated above, L-γ-glutamylamine cyclotransferase is the only enzyme which catalyzes conversion of L-γ-glutamyl compounds to 5-oxoproline. Since the hydrolysis of the $N^\alpha$positional isomer of (L-γ-glutamyl)-L-lysine is not catalyzed by L-γ-glutamylamine cyclotransferase, it is possible to distinguish between GC-MS results from the $N^\alpha$positional isomer and the $N^\epsilon$positional isomer (which is intended to be measured).

Thus, loss of the $N^\epsilon$-(L-γ-glutamyl)-L-lysine signal after treatment with L-γ-glutamylamine cyclotransferase will be strong evidence that the (L-γ-glutamyl)-L-lysine being measured is the $N^\epsilon$ positional isomer rather than the $N^\alpha$ positional isomer.

Once the test solution has been prepared, the gas chromatography-mass spectrometry analysis of the test solution is performed to determine the concentration of $N^\epsilon$-(L-γ-glutamyl)-L-lysine. The preferred test conditions (i.e., temperature, injector volume, and gas flow rate) can be adjusted and optimized according to the type of gas chromatographic and mass spectrometry equipment a particular lab employs. The gas is preferably an inert gas such as helium.

Given the quantity of the isotope-labeled $N^\epsilon$-(L-γ-glutamyl)-L-lysine introduced into the test solution, the concentration of $N^\epsilon$-(L-γ-glutamyl)-L-lysine ($X_2$) in the test solution (and, thus, the sample) can be calculated according to Equation 4 below:

$$X_2 = ((C_1/C_2) - 1) \cdot X_1 \quad \text{(Eq. 4)}$$

(*Kamen Isotopic Tracers in Biology*, 3d ed., Academic Press (New York), p. 177, which is hereby incorporated by reference), where $X_1$ is the amount of internal standard (e.g., isotope-labeled $N^\epsilon$-(L-γ-glutamyl)-L-lysine) introduced into the test solution, $C_1$ is the relative enrichment of the isotope-labeled $N^\epsilon$-(L-γ-glutamyl)-L-lysine added to the test solution, and $C_2$ is the relative enrichment measured after adding isotope-labeled $N^\epsilon$-(L-γ-glutamyl)-L-lysine to the test solution.

Once the concentration of $N^\epsilon$-(L-γ-glutamyl)-L-lysine has been determined for a sample, this is compared to a normal or standard concentration of $N^\epsilon$-(L-γ-glutamyl)-L-lysine (i.e., control) which is determined in a similar manner using samples obtained from individuals known to be asymptomatic for $(CAG)_n/Q_n$-expansion disorders. If the concentration of $N^\epsilon$-(L-γ-glutamyl)-L-lysine is significantly higher statistically than the normal or standard concentration of $N^\epsilon$-(L-γ-glutamyl)-L-lysine, within experimentally determined confidence limits, then the individual can be diagnosed as positive for a $(CAG)_n/Q_n$-expansion disorder.

A number of $(CAG)_n/Q_n$-expansion disorders have presently been identified and others are likely to be identified in the future. Exemplary $(CAG)_n/Q_n$-expansion disorders, which can be diagnosed or assessed by the present invention, and the encoded proteins include: Huntington's Disease, huntingtin; denatorubral pallidoluysian atrophy, strophin; spinobulbar muscular atrophy, androgen receptor; spinocerebellar ataxia-3, ataxin-3; spinocerebellar ataxia-6, Purkinje cell-specific $Ca^{2+}$ channel subunit $\alpha_{1A}$; spinocerebellar ataxia-1, ataxin-1; spinocerebellar ataxia-2, ataxin-2; and spinocerebellar ataxia-7, ataxin-7. In each of these disorders, progressive impairment of coordination and/or motor neuron degeneration is associated with variable mental symptoms (Paulson et al., "Trinucleotide Repeats in Neurogenetics Disorders," *Annu. Rev. Neurosci.* 19:79–107 (1996); Lunkes et al., "Polyglutamines, Nuclear Inclusions and Neurodegeneration," *Nat. Med.* 3:1201–1202 (1997); Schöls et al., "Autosomal Dominant Cerebellar Ataxia: Phenotypic Differences in Genetically Defined Subtypes," *Ann Neurol.* 42:924–932 (1997), which are hereby incorporated by reference).

In addition to diagnosing an individual as positive for a $(CAG)_n/Q_n$-expansion disorder, it is also possible to gauge progression of a $(CAG)_n/Q_n$-expansion disorder within a single patient. In comparison to diagnosing an individual (i.e., comparing $N^\epsilon$-(L-γ-glutamyl)-L-lysine concentration in a sample to a standard), monitoring progression of the $(CAG)_n/Q_n$-expansion disorder can be performed by measuring multiple (i.e., two or more) GC-MS analyses on samples taken from the same patient over a course of time.

Therefore, another aspect of the present invention relates a method of measuring progression of a $(CAG)_n/Q_n$-expansion disorder. This method is performed by obtaining a sample from an individual and determining a concentration of $N^\epsilon$-(L-γ-glutamyl)-L-lysine in the sample. At a later time, this is repeated. (i.e., obtaining a second sample from the individual and determining a concentration of $N^\epsilon$-(L-γ-glutamyl)-L-lysine in the second sample). Progression of a $(CAG)_n/Q_n$-expansion disorder is indicated by the second concentration being higher, to a statistical significance, than the first concentration.

Since disease progression must be measured over time, the second sample should be obtained at least one day after obtaining the first sample. More preferably, the taking of samples is at least one week apart. Since disease progression may occur over the course of years, it is contemplated that one or more months, or even years, separate obtaining the first and second samples. Moreover, it is possible to compare multiple samples taken over the course of time following diagnosis. For example, it is possible to chart $(CAG)_n/Q_n$-expansion disorder progression using the results of multiple GC-MS analyses. This will indicate the change in $N^\epsilon$-(L-γ-glutamyl)-L-lysine concentration in fluid samples taken over the entire course of disease progression.

Because new therapeutic treatments are continually being developed, it is critical to determine the efficacy of those treatments. Many times, assessment of therapeutic treatments is performed using a subjective evaluation of a patient. This is often sufficient to gauge generally how a patient is responding to a treatment. Subjective analyses, however, are inherently less reliable than an objective test. The present invention provides an objective test for determining the efficacy of a therapeutic treatment provided to a patient.

Therefore, a further aspect of the invention relates to a method of measuring therapeutic efficacy of a treatment for a $(CAG)_n/Q_n$-expansion disorder. This method is performed by obtaining a sample from an individual and then determining a concentration of $N^\epsilon$-(L-γ-glutamyl)-L-lysine in the sample. After determining the base concentration of $N^\epsilon$-(L-γ-glutamyl)-L-lysine, the individual is provided with a treatment for a $(CAG)_n/Q_n$-expansion disorder. Subsequent to receiving the treatment, a second sample is obtained from the individual and the concentration of $N^\epsilon$-(L-γ-glutamyl)-L-lysine in the second sample is determined. By comparing the later-determined concentration of $N^\epsilon$-(L-γ-glutamyl)-L-lysine to the earlier-determined concentration of $N^\epsilon$-(L-γ-glutamyl)-L-lysine, it is possible to measure or assess the therapeutic efficacy of the treatment that the individual received during the time between obtaining the samples.

A number of therapeutic treatments for $(CAG)_n/Q_n$ disorders have been described in the art and new therapeutic treatments are continually being developed. The present invention can be used to identify the efficacy of previously known or suspected treatments or treatments developed in the future. Exemplary known or suspected therapeutic agents for treatment of HD include, but are not limited to, (1) glial cell line-derived neurotrophic factor (Araujo et al., "ret Receptor Tyrosine Kinase Immunoreactivity is Altered in Glial Cell Line-derived Neurotrophic Factor-responsive Neurons Following Lesions of the Nigrostriatal and Septo-hippocampal Pathways," *Neuroscience* 80(1):9–16 (1997), which is hereby incorporated by reference), (2) agonists of metabotropic glutamate receptors (Grauer and Marquis, "Intracerebral Administration of Metabotropic Glutamate Receptor Agonists Disrupts Prepulse Inhibition of Acoustic Startle in Sprague-Dawley Rats," *Psychopharmacology* 141 (4):405–412 (1999), which is hereby incorporated by reference), and (3) coenzyme Q (Koroshetz et al., "Energy Metabolism Defects in Huntington's Disease and Effects of Coenzyme Q10," *Ann. Neurol.* 41(2):160–165 (1997), which is hereby incorporated by reference). An exemplary known or suspected therapeutic agents for treatment of spinocerebellar ataxia includes, but is not limited to, D-serine ethylester (Department of Degenerative Neurological Diseases (Tokyo, Japan), "The Stereo-specific Effect of D-serine Ethylester and the D-cycloserine in Ataxic Mutant Mice," *Brain Res.* 808(1):42–47 (1998), which is hereby incorporated by reference).

The therapeutic efficacy of treatment will, of course, vary from treatment to treatment and efficacy will not necessarily be determined solely by a decrease in the concentration of $N^\epsilon$-(L-γ-glutamyl)-L-lysine from the earlier-obtained sample to the later-obtained sample. For instance, maintaining the status quo may be indicative of an effective treatment for some $(CAG)_n/Q_n$-expansion disorders, whereas simply reducing the rate (change/time) at which the concentration of $N^\epsilon$-(L-γ-glutamyl)-L-lysine changes over the course of successive sample collection and $N^\epsilon$-(L-γ-glutamyl)-L-lysine measurements.

These aspects of the present invention are further illustrated by the examples below.

EXAMPLES

The following examples are provided to illustrate embodiments of the present invention, but they are by no means intended to limit its scope.

Example 1

Preparation of $N^\epsilon$-(L-γ-glutamyl)-L-[α-$^{15}$N]lysine $N^\epsilon$-(L-γ-Glutamyl)-L-lysine was obtained from Sigma Chemical Co. Except as noted, reagents for the synthesis of $^{15}$N-labeled lysine were obtained from Aldrich Chemical Company. Bovine kidney L-γ-glutamylamine cyclotransferase was prepared according to the method of Fink and Folk (Fink and Folk, "γ-Glutamylamine Cyclotransferase (rabbit kidney)," *Methods Enzymol.* 94:347–351 (1983), which is hereby incorporated by reference). The specific activity of the preparation using $N^\epsilon$-(L-γ-glutamyl)-L-lysine as substrate was 2.1 μmol/h.mg$^{-1}$ protein; 37° C. (Fink and Folk, "γ-Glutamylamine Cyclotransferase (rabbit kidney)," *Methods Enzymol.* 94:347–351 (1983), which is hereby incorporated by reference). The preparation is devoid of (L-γ-glutamyl)-L-amino acid cyclotransferase and L-γ-glutamyltranspeptidase activities.

Ethyl chloroformate (0.144 ml, 1.5 mmol) was added dropwise with stirring to a solution of benzyloxycarbonyl-L-glutamic acid-α-benzyl ester (0.557 g. 1.5 mmol) and tri-n-butylamine (0.36 ml, 1.5 mmol) in 1.5 ml of tetrahydrofuran maintained at 0° C. Stirring was continued at 0° C. for 30 minutes, at which time were added dropwise a solution of tri-n-butylamine (0.43 ml, 1.8 mmol) in 1.5 ml of tetrahydrofuran and a solution of the copper salt of L-[α-$^{15}$N(95%)lysine.2HCL.H$_2$O (Cambridge Isotope laboratories, lot BI-1125; 0.355 g, 1.5 mmol). The copper salt of L-[α-$^{15}$N(95%)lysine.2HCL.H$_2$O was prepared by refluxing its solution in 1.5 ml of water with basic copper carbonate ($CuCO_3.Cu(OH)_2$; 0.2 g, 0.9 mmol) for 20 minutes, cooling and combining the clear filtrate with 1 ml water wash of the excess basic copper carbonate.

The reaction mixture was stirred for 30 minutes at 0° C., followed by 4 hours at room temperature. After standing overnight, the mixture was diluted with 15 ml of water. The precipitate which formed was removed and washed well with water, triturated with ethyl acetate and suspended in 10 ml of water-ethanol (1:1, v/v). Hydrogen sulfide gas was passed through the mixture for 15 minutes and stirring was continued for an additional two hours. Passage of gas and stirring were repeated. The mixture was heated gently, filtered through a thick layer of "filter aid" and taken to dryness in vacuo.

The residue was dissolved in 15 ml of water-ethanol (1:1, v/v), 1 ml of glacial acetic acid was added and hydrogenation was conducted for 4 hours with 0.1 g of palladium black at 40 lbs/in$^2$. The catalyst was removed by filtration and the solvents removed in vacuo. The crystalline product was re-crystallized from water-ethanol to yield 60 mg (15% overall yield). Thin layer chromatography; $R_f$ 0.13, 1-propanol/H$_2$O) (7:3, v/v); $R_f$ 0.60, CH$_3$Cl$_3$/CH$_3$OH/NH$_4$OH (2:2:1, v/v/v; silica gel plates, detection with ninhydrin spray). The $R_f$ values of $N^\epsilon$-(L-γ-glutamyl)-L-[α-$^{15}$N]lysine were identical to those exhibited by authentic $N^\epsilon$-(L-γ-glutamyl)-L-lysine.

Example 2

Comparison of $N^\epsilon$-(L-γ-glutamyl)-L-[α-$^{15}$N]lysine and $N^\epsilon$-(L-γ-glutamyl)-L-lysine Mass Spectometry Results Carboxethylester derivatives of $N^\epsilon$-(L-γ-glutamyl)-L-[-α-$^{15}$N]lysine and $N^\epsilon$-(L-γ-glutamyl)-L-lysine were prepared using standard procedures. Solutions containing the resulting products were individually injected into a GC-MS system for analysis.

Figure 1:
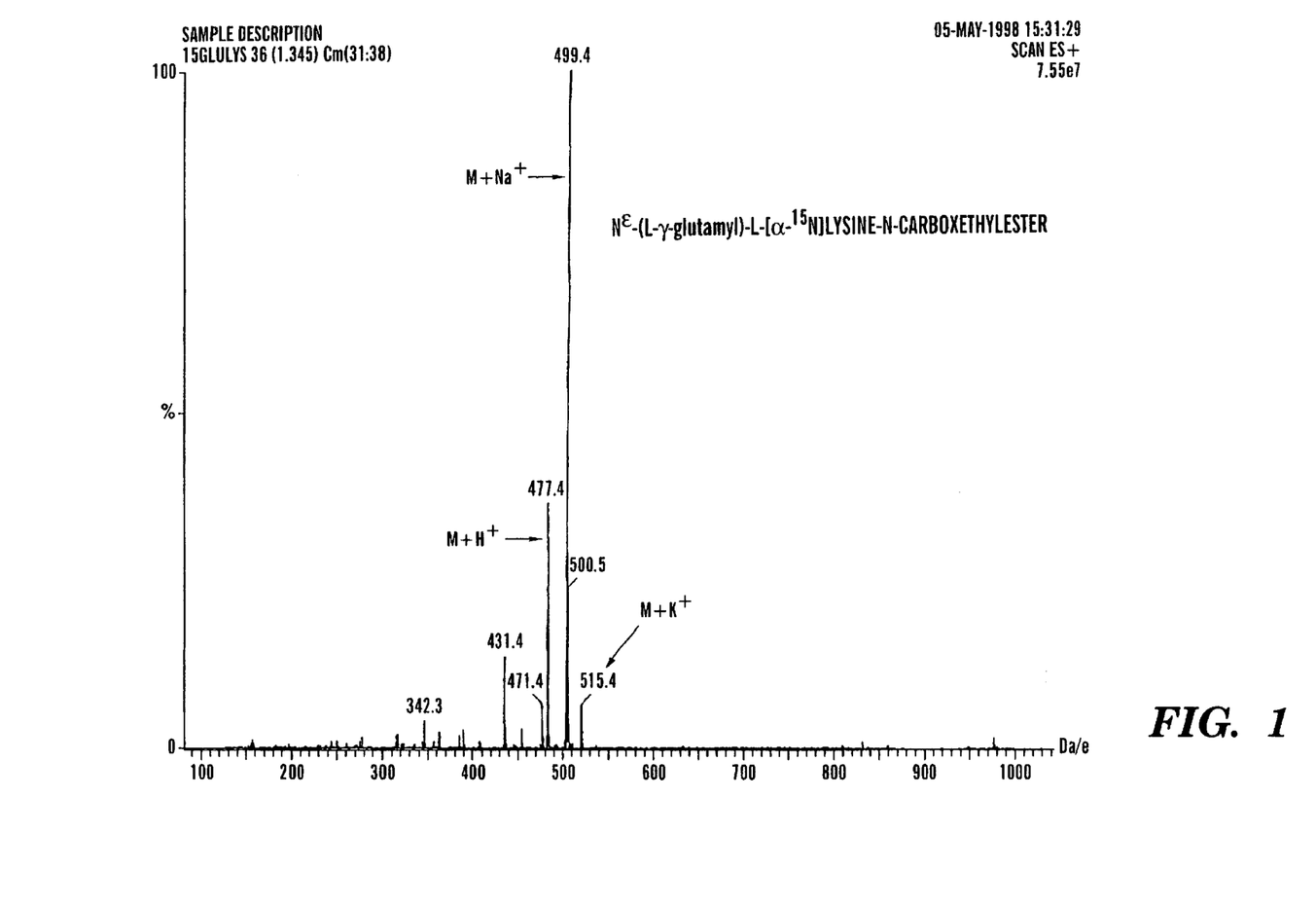
FIG. 1 is an image of a mass spectral analysis of the carboxyethylester of $N^\epsilon$-(L-γ-glutamyl)-L-[α-$^{15}$N]lysine.
Figure 2:
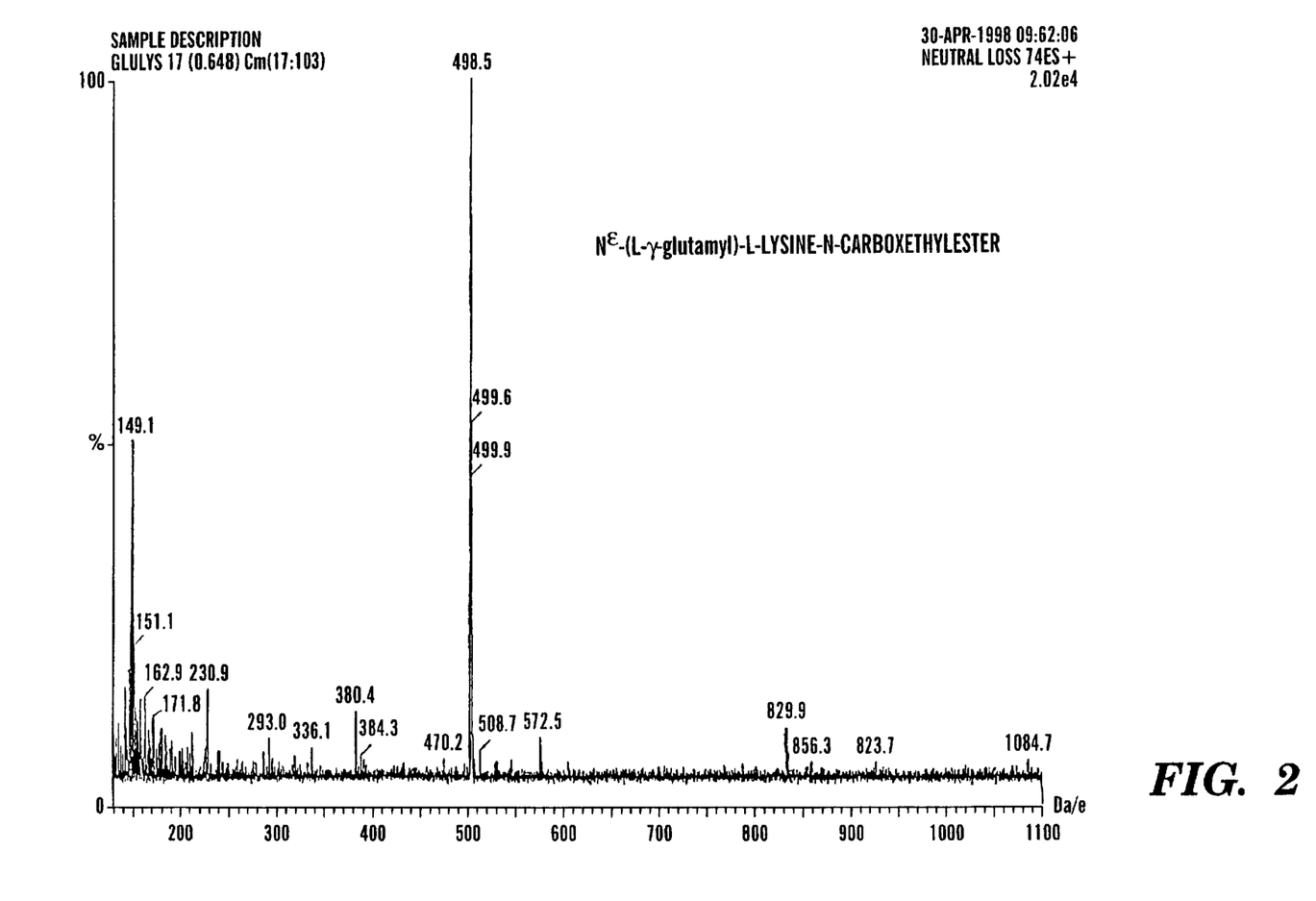
FIG. 2 is an image of a mass spectral analysis of the carboxyethylester of $N^\epsilon$-(L-γ-glutamyl)-L-lysine.

The resulting mass spectral analyses are shown in FIGS. 1 and 2 for the carboxyethylesters of $N^\epsilon$-(L-γ-glutamyl)-L-[α-$^{15}$N]lysine and $N^\epsilon$-(L-γ-glutamyl)-L-lysine, respectively. A comparison of FIGS. 1 and 2 shows the effect of the [α-$^{15}$N]lysine on the spectral properties, with an approximately one mass unit shift for the M+Na$^+$ peak from 498.5 to 499.4. This indicates that $N^\epsilon$-(L-γ-glutamyl)-L-[α-$^{15}$N] lysine is sufficient for use as an internal standard to samples containing $N^\epsilon$-(L-γ-glutamyl)-L-lysine.

Example 3

Measurement of $N^\epsilon$-(L-γ-glutamyl)-L-lysine in Cerebrospinal Fluid from Huntington's Disease Patients Cerebrospinal fluid samples were obtained from 5 patients diagnosed with Huntington's Disease and 9 control patients using standard procedure. Approximately 1 ml samples were withdrawn into polypropylene tubes. After collecting the CSF samples, they were then frozen at −80° C. until performance of the GC-MS analysis.

The CSF samples were thawed and a solution containing the internal standard $N^\epsilon$-(L-γ-glutamyl)-L-[α-$^{15}$N]lysine was introduced. Following addition of the internal standard solution, the test solutions were injected into a gas chromatographic column for GC-MS analysis.

The presence of $N^\epsilon$-(L-γ-glutamyl)-L-lysine and $N^\epsilon$-(L-γ-glutamyl)-L-[α-$^{15}$N]lysine were observable by viewing the M/Z peak and peak heights were measured, as indicated in the table below (arbitrary units).

The CSF concentration of $N^\epsilon$-(L-γ-glutamyl)-L-lysine was calculated for each of the individuals tested according to Equation 4, infra. Individuals (1)–(9) are control patients and individuals (10)–(14) are those diagnosed with Huntington's Disease.

TABLE 1

$N^\epsilon$-(L-γ-glutamyl)-L-lysine Concentrations in CSF of Control and HD Patients

| Individual | Individual Peak Height (Arbitrary units) | CSF $N^\epsilon$-(L-γ-glutamyl)-L-lysine (μM) |
|---|---|---|
| 1 | 677 | 0.68 |
| 2 | 2024 | 2.02 |
| 3 | 1871 | 1.87 |
| 4 | 3360 | 3.35 |
| 5 | 739 | 0.74 |
| 6 | 1299 | 1.30 |
| 7 | 1100 | 1.10 |
| 8 | 359 | 0.36 |
| 9 | 557 | 0.56 |
| Average | 1332 ± 318 | 1.3 ± 0.32 |
| Range | 359–3360 | 0.36–3.35 |
| 10 | 832 | 0.83 |
| 11 | 3791 | 3.80 |
| 12 | 4154 | 4.16 |
| 13 | 3051 | 2.05 |
| 14 | 2156 | 2.16 |
| Average | 2797 ± 596 | 2.80 ± 0.60 |
| Range | 832–4154 | 0.83–4.16 |

Test results were analyzed by Mann Whitney U test utilizing the software program Sigma Stat.

As shown in the table above, the range of $N^\epsilon$-(L-γ-glutamyl)-L-lysine concentrations varied between 0.36 and 3.35 μM for control individuals and 0.83 and 4.16 μM for HD patients. Excluding the highest score for the control group (3.35 μM) and the lowest score for the HD group (0.83 μM), the ranges did not otherwise overlap (i.e., 0.36–2.02 μM for the control group versus 2.05–4.16 μM for the HD group). Even without excluding the extreme scores in each group, there was a statistically significant difference ($p=0.025$) in the average $N^\epsilon$-(L-γ-glutamyl)-L-lysine concentrations in CSF samples of HD patients and control individuals. These differences show that $N^\epsilon$-(L-γ-lysine concentrations can be used as a reliable marker for diagnosing $(CAG)_n/Q_n$-expansion disease.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of diagnosing a $(CAG)_n/Q_n$-expansion disorder in an individual, said method comprising:
    obtaining a sample from an individual;
    combining the sample with o-phthaldialdehyde under conditions effective to form a test solution comprising an o-phthaldialdehyde derivative of $N^\epsilon$-(L-γ-glutamyl)-L-lysine; and
    determining whether the test solution contains a concentration of the o-phthaldialdehyde derivative of $N^\epsilon$-(L-γ-glutamyl)-L-lysine which is elevated in comparison to a normal concentration of the o-phthaldialdehyde derivative of $N^\epsilon$-(L-γ-glutamyl)-L-lysine, wherein an elevated concentration in the test solution indicates that the individual has a $(CAG)_n/Q_n$-expansion disorder.

2. The method according to claim 1, wherein the sample is cerebrospinal fluid, blood, or urine.

3. The method according to claim 1, wherein said determining comprises:
    performing high performance liquid chromatography with coularray detection on the test solution under conditions effective to determine the concentration of the o-phthaldialdehyde derivative of $N^\epsilon$-(L-γ-glutamyl)-L-lysine.

4. The method according to claim 1, wherein said combining further comprises:
    introducing L-γ-glutamylamine cyclotransferase into the test solution.

5. The method according to claim 1, wherein the $(CAG)_n/Q_n$-expansion disorder is a neurodegenerative disorder.

6. The method according to claim 5, wherein the neurodegenerative disorder is selected from the group of Huntington's Disease, denatorubral pallidoluysian atrophy, spinobulbar muscular atrophy, spinocerebellar ataxia-3, spinocerebellar ataxia-6, spinocerebellar ataxia-1, spinocerebellar ataxia-2, and spinocerebellar ataxia-7.

7. A method of measuring progression of a $(CAG)_n/Q_n$-expansion disorder, said method comprising:
    obtaining a first sample from an individual;
    combining the first sample with o-phthaldialdehyde under conditions effective to form a first test solution comprising an o-phthaldialdehyde derivative of $N^\epsilon$-(L-γ-glutamyl)-L-lysine;
    determining a first concentration of the o-phthaldialdehyde derivative of $N^\epsilon$-(L-γ-glutamyl)-L-lysine in the first test solution;
    obtaining a second sample from the individual at a time after the first sample is obtained;
    combining the second sample with o-phthaldialdehyde under conditions effective to form a second test solution comprising the o-phthaldialdehyde derivative of $N^\epsilon$-(L-γ-glutamyl)-L-lysine; and
    determining a second concentration of the o-phthaldialdehyde derivative of $N^\epsilon$-(L-γ-glutamyl)-L-lysine in the second test solution;
    wherein progression of a $(CAG)_n/Q_n$-expansion disorder is indicated by the second concentration being higher than the first concentration.

8. The method according to claim 7, wherein the first and second samples are cerebrospinal fluid, blood, or urine, with the first and second samples being the same fluid type.

9. The method according to claim 7, wherein each said determining comprises:
    performing high performance liquid chromatography with coularray detection on the first or second test solution under conditions effective to determine the concentration of the o-phthaldialdehyde derivative of $N^\epsilon$-(L-γ-glutamyl)-L-lysine.

10. The method according to claim 7, wherein each said combining further comprises:
    introducing L-γ-glutamylamine cyclotransferase into the first or second test solution.

11. The method according to claim 7, wherein the $(CAG)_n/Q_n$-expansion disorder is a neurodegenerative disorder.

12. The method according to claim 11, wherein the neurodegenerative disorder is selected from the group of Huntington's Disease, denatorubral pallidoluysian atrophy, spinobulbar muscular atrophy, spinocerebellar ataxia-3, spinocerebellar ataxia-6, spinocerebellar ataxia-1, spinocerebellar ataxia-2, and spinocerebellar ataxia-7.

13. The method according to claim 7, wherein said obtaining a second sample is performed at least one day after said obtaining a first sample.

14. A method of measuring therapeutic efficacy of a treatment for a $(CAG)_n/Q_n$-expansion disorder, said method comprising:

obtaining a first sample from an individual;

combining the first sample with o-phthaldialdehyde under conditions effective to form a first test solution comprising an o-phthaldialdehyde derivative of $N^\epsilon$-(L-γ-glutamyl)-L-lysine;

determining a first concentration of the o-phthaldialdehyde derivative of $N^\epsilon$-(L-γ-glutamyl)-L-lysine in the first test solution;

providing the individual with a treatment for a $(CAG)_n/Q_n$-expansion disorder;

obtaining a second sample from the individual after said providing the individual with a treatment;

combining the second sample with o-phthaldialdehyde under conditions effective to form a second test solution comprising the o-phthaldialdehyde derivative of $N^\epsilon$-(L-γ-glutamyl)-L-lysine; and determining a second concentration of the o-phthaldialdehyde derivative of $N^\epsilon$-(L-γ-glutamyl)-L-lysine in the second test solution; and comparing the second concentration to the first concentration to measure the therapeutic efficacy of the treatment for a $(CAG)_n/Q_n$-expansion disorder, wherein an effective treatment is indicated by the second concentration being lower than the first concentration.

15. The method according to claim 14, wherein the first and second samples cerebrospinal fluid, blood, or urine, with the first and second samples being the same fluid type.

16. The method according to claim 14, wherein each said determining comprises:

performing high performance liquid chromatography with coularray detection on the first or second test solution under conditions effective to determine the concentration of the o-phthaldialdehyde derivative of $N^\epsilon$-(L-γ-glutamyl)-L-lysine.

17. The method according to claim 14, wherein each said combining further comprises:

introducing L-γ-glutamylamine cyclotransferase into the first or second test solution.

18. The method according to claim 14, wherein the $(CAG)_n/Q_n$-expansion disorder is a neurodegenerative disorder.

19. The method according to claim 18, wherein the neurodegenerative disorder is selected from the group of Huntington's Disease, denatorubral pallidoluysian atrophy, spinobulbar muscular atrophy, spinocerebellar ataxia-3, spinocerebellar ataxia-6, spinocerebellar ataxia-1, spinocerebellar ataxia-2, and spinocerebellar ataxia-7.

20. The method according to claim 14, wherein said obtaining a second sample is performed more than one day after said obtaining a first sample.

* * * * *

UNITED STATES PATENT AND TRADEMARK OFFICE
CERTIFICATE OF CORRECTION

PATENT NO.       : 6,548,243 B1
APPLICATION NO.  : 09/743590
DATED            : April 15, 2003
INVENTOR(S)      : Cooper et al.

It is certified that error appears in the above-identified patent and that said Letters Patent is hereby corrected as shown below:

Col. 1 at lines 6-9, delete "This invention was made in part with support by the U.S. Government under Grant No. 5R35 AG09014 (Lead Award) from the National Institute of Health. The U.S. Government may have certain rights in this invention." and insert --This invention was made with government support under grant 5R35 AG09014 (Lead Award) awarded by National Institutes of Health. The government has certain rights in the invention-- in its place.

Signed and Sealed this

Fourteenth Day of April, 2009

JOHN DOLL
*Acting Director of the United States Patent and Trademark Office*